United States Patent

Asano et al.

[11] Patent Number: 6,027,527
[45] Date of Patent: Feb. 22, 2000

[54] STENT

[75] Inventors: Hiroyuki Asano; Ichizo Okata, both of Yokohama, Japan

[73] Assignee: Piolax Inc., Kanagawa-ken, Japan

[21] Appl. No.: 08/986,060

[22] Filed: Dec. 5, 1997

[30] Foreign Application Priority Data

Dec. 6, 1996 [JP] Japan .................................... 8-342512
Jan. 24, 1997 [JP] Japan .................................... 9-026015

[51] Int. Cl.$^7$ ................................................. A61F 2/06
[52] U.S. Cl. ............................................ 623/1; 623/12
[58] Field of Search ...................... 627/1, 12; 606/108, 606/192, 194

[56] References Cited

U.S. PATENT DOCUMENTS

| | | | |
|---|---|---|---|
| 4,739,762 | 4/1988 | Palmaz | 623/1 |
| 5,695,516 | 12/1997 | Fischell et al. | 606/194 |
| 5,697,971 | 12/1997 | Fischell et al. | 623/1 |
| 5,755,776 | 5/1998 | Al-Saadon | 623/1 |
| 5,776,161 | 7/1998 | Globerman | 623/1 |
| 5,776,181 | 7/1998 | Lee et al. | 623/1 |
| 5,817,126 | 10/1998 | Imran | 623/1 |

FOREIGN PATENT DOCUMENTS

| | | |
|---|---|---|
| 4-37445 | 3/1992 | Japan . |
| 4-256759 | 9/1992 | Japan . |
| 6-44910 | 6/1994 | Japan . |
| 6-181993 | 7/1994 | Japan . |

*Primary Examiner*—Bruce E. Snow
*Attorney, Agent, or Firm*—Ladas & Parry

[57] ABSTRACT

A stent having a cylindrical shape includes frame-like unexpandable portions incapable of being expanded in a circumferential direction, and frame-like expandable portions capable of being expanded in the circumferential direction. The unexpandable portions and the expandable portions are alternately connected together in the circumferential direction.

15 Claims, 5 Drawing Sheets

STENT

BACKGROUND OF THE INVENTION

1. Field of the Invention

This invention relates to a stent adapted to be inserted into a tubular organ of the human body such as a blood vessel or a ureter to thereby maintain the lumen of the tubular organ open.

2. Related Background Art

For example, in case of the remedy of myocardial infarction or the like, it is practiced to insert an expanding tool called a stent into the strictured portion of a blood vessel, and prevent the obstruction of the blood vessel. Also, in case of the remedy of a ureteric calculus or the like, a stent is sometimes used to maintain the ureter expanded to make the calculus easy to be discharged.

Generally, the stent in its shape of reduced diameter is mounted on the outer periphery of the tip end portion of a balloon catheter and is inserted into a blockaded affected part through a guide catheter, whereafter the baloon of the balloon catheter is inflated and is forcibly widened, and in that state, it is detained in the blockaded affected part to thereby expand the tubular organ.

As an example of the stent of the prior art, Japanese Laid-Open Patent Application No. 6-181993 discloses a stent comprising a plurality of cylindrical elements in dependently expandable in the radial direction thereof and connected together so as to be substantially aligned in a common axis, said plurality of cylindrical elements being connected together with flexibility in the lengthwise direction thereof. Also, as an example of it, there is disclosed a stent comprising a plurality of cylinder elements circumferentially extending in a waveform and annularly connected together, said plurality of cylinder elements being axially arranged at predetermined intervals, portions of these cylinder elements being connected together by an axially extending mutual connecting element.

The stent of Japanese Laid-Open Patent Application No. 6-181993, however, is of such structure that the interval between respective line portions becomes wider uniformly when the cylinder elements forming a waveform are expanded. In such structure, the inner wall surface of a soft tubular organ such as a blood vessel could not be satisfactorily supported by the cylinder elements roughly arranged because the cylinder elements would be got into the inner wall of the tubular organ, and this has led to the undesirable possibility that after the detention, the inside skin increases from this gap, thus causing stricture again.

Japanese Patent Publication No. 6-44910 discloses a stent molded into the form of a snake including a series of straight portions and a plurality of bent portions, said straight portions being coupled together by said bent portions and forming a series of staggered loops, said form of a snake being molded into a cylindrical shape having a longitudinal axis, said straight portions comprising a plastically deformable wire surrounding said axis and bent into a substantially cylindrical form perpendicular to said axis.

However, in the stent disclosed in Japanese Patent Publication No. 6-44910, the straight portions are simply bent into a C-shape as viewed from the end surface thereof and therefore, in addition to the problems raised in Japanese Laid-Open Patent Application No. 6-181993, the holding force after expansion is weak, and this has led to the undesirable possibility that the diameter thereof is reduced by the pressure of the inner wall of a blood vessel, thus causing reconstriction.

SUMMARY OF THE INVENTION

Accordingly, it is the object of the present invention to provide a stent capable of eliminating any possible occurrence of the constriction after expansion thereof.

The stent according to the present invention has frame-like unexpandable portions incapable of being expanded in a circumferential direction, and frame-like expandable portions capable of being expanded in the circumferential direction, and has a cylindrical shape in which said unexpandable portions and said expandable portions are alternately connected together in the circumferential direction.

According to an embodiment of the stent of the present invention, said unexpandable portions each comprise a triangular frame, one side of which extends along the circumferential direction of said stent.

According to an embodiment of the stent of the present invention, said expandable portions each are constructed into a frame-like shape by first sides extending along the circumferential direction and opposed to each other in the axial direction, and second sides extending in the axial direction and opposed to each other in the circumferential direction, and said frame is constructed so that in the diameter-reduced state of said stent, the second sides of said frame may be curved inwardly thereof, and in the diameter-enlarged state of said stent, the second sides of said frame may be curved outwardly thereof.

According to an embodiment of the stent of the present invention, said expandable portions each are constructed into a frame-like shape by first sides extending in the circumferential direction and opposed to each other in the axial direction, and second sides extending in the axial direction and opposed to each other in the circumferential direction, and said frame is constructed so that in the diameter-reduced state of said stent, the second sides may be replaced relative to the first sides, the first side and the second side of said frame may form an acute angle and the first side and the second side of said frame may form an obtuse angle, whereby said stent may be expanded in its diameter.

As described above, according to an embodiment of the present invention, the frame constituting the expandable portions is designed such that a pair of sides (second sides) opposed to each other in the circumferential direction are greatly displaced in the circumferential direction relative to a pair of sides (first sides) opposed to each other in the axial direction without the positions of the first sides being displaced even after the expansion of the stent and therefore, the degree of expansion of the stent can be made great, while on the other hand, the change in the axial length of the stent before and after the expansion thereof scarcely occurs or can be suppressed to a negligible degree.

According to an embodiment of the stent of the present invention, the expandable portions each comprise a lozenge-shaped frame of which the diagonals extend along the axial direction and circumferential direction of the stent, and this frame is constructed such that in the diameter-reduced state of the stent the diagonal in the axial direction is longer than the diagonal in the circumferential direction and that in the diameter-expanded state of the stent, the diagonal in the circumferential direction is longer than the diagonal in the axial direction.

According to an embodiment of the stent of the present invention, the end portions of the sides of the triangular frame of each of the unexpandable portions extending along the circumferential direction and the second sides (the sides opposed to each other in the circumferential direction) of the frame of each of the expandable portions are connected together, and the expandable portions and the unexpandable portions are alternately connected together in the circumferential direction.

According to an embodiment of the stent of the present invention, an X-shaped beam for connecting the first sides opposed to each other in the axial direction together is provided in the interior of the frame of each of the expandable portions and therefore, the inner wall of a tubular organ can be supported by a wider area to thereby prevent the tissue of the inner wall of the tubular organ from coming into the inside and propagating and as the result, reconstriction can be prevented.

According to an embodiment of the stent of the present invention, the unexpandable portions are connected together in an axial direction, whereby unexpandable portion columns and expandable portion columns extending in the axial direction are alternately disposed in the circumferential direction.

While the material of the stent of the present invention is not particularly restricted, a metal such as stainless steel, tantalum, titanium, platinum, gold, tungsten or a shape memory alloy is preferable. The stent of the present invention can be manufactured, for example, by making a cylindrical member of one of the above-mentioned metals, and cutting this cylindrical member into a predetermined pattern by such means as etching or laser working.

DESCRIPTION OF THE PREFERRED EMBODIMENTS

Figure 1:
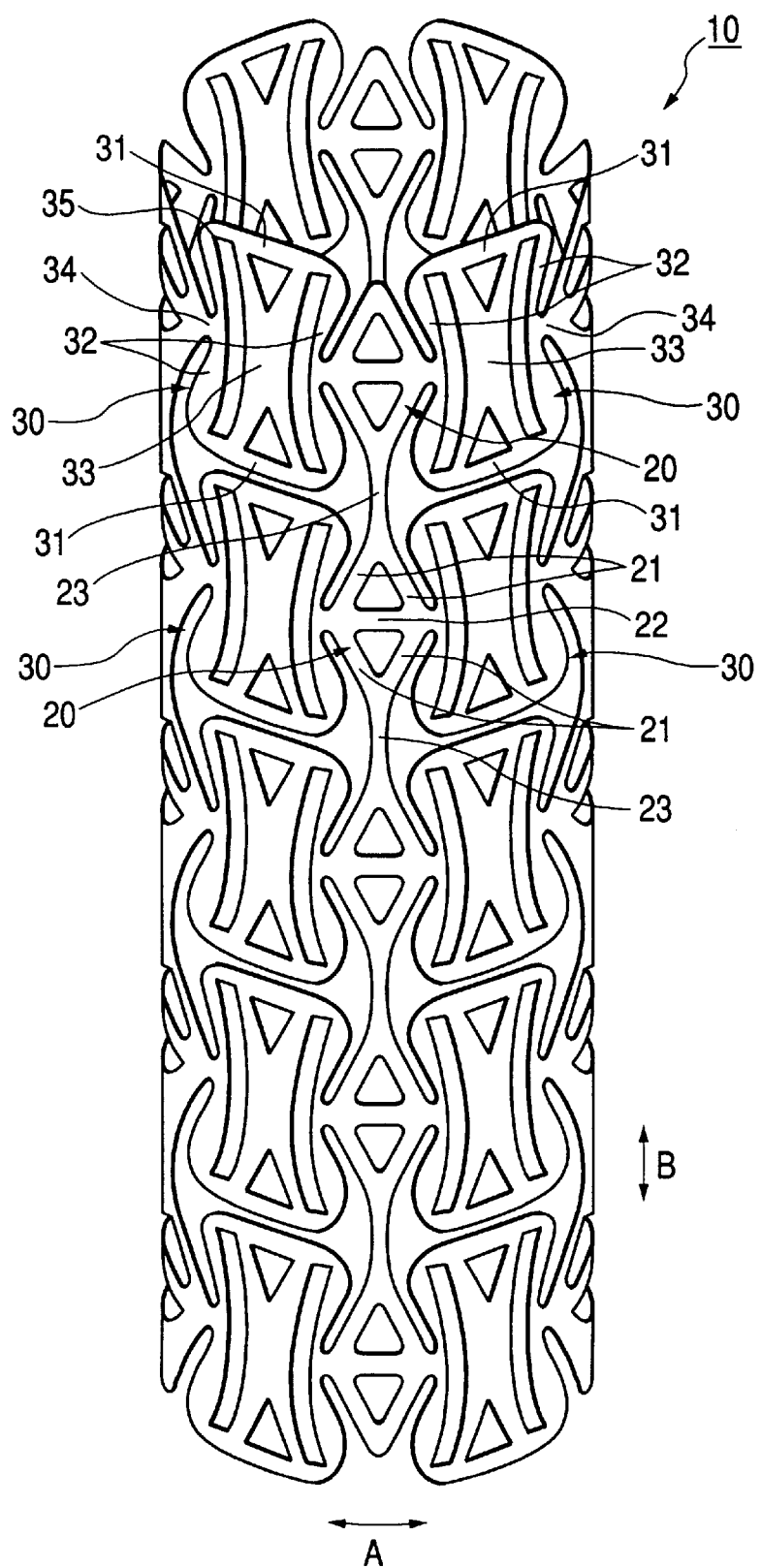
FIG. 1 is a perspective view showing an embodiment of the stent of the present invention in its diameter-reduced state.
Figure 2:
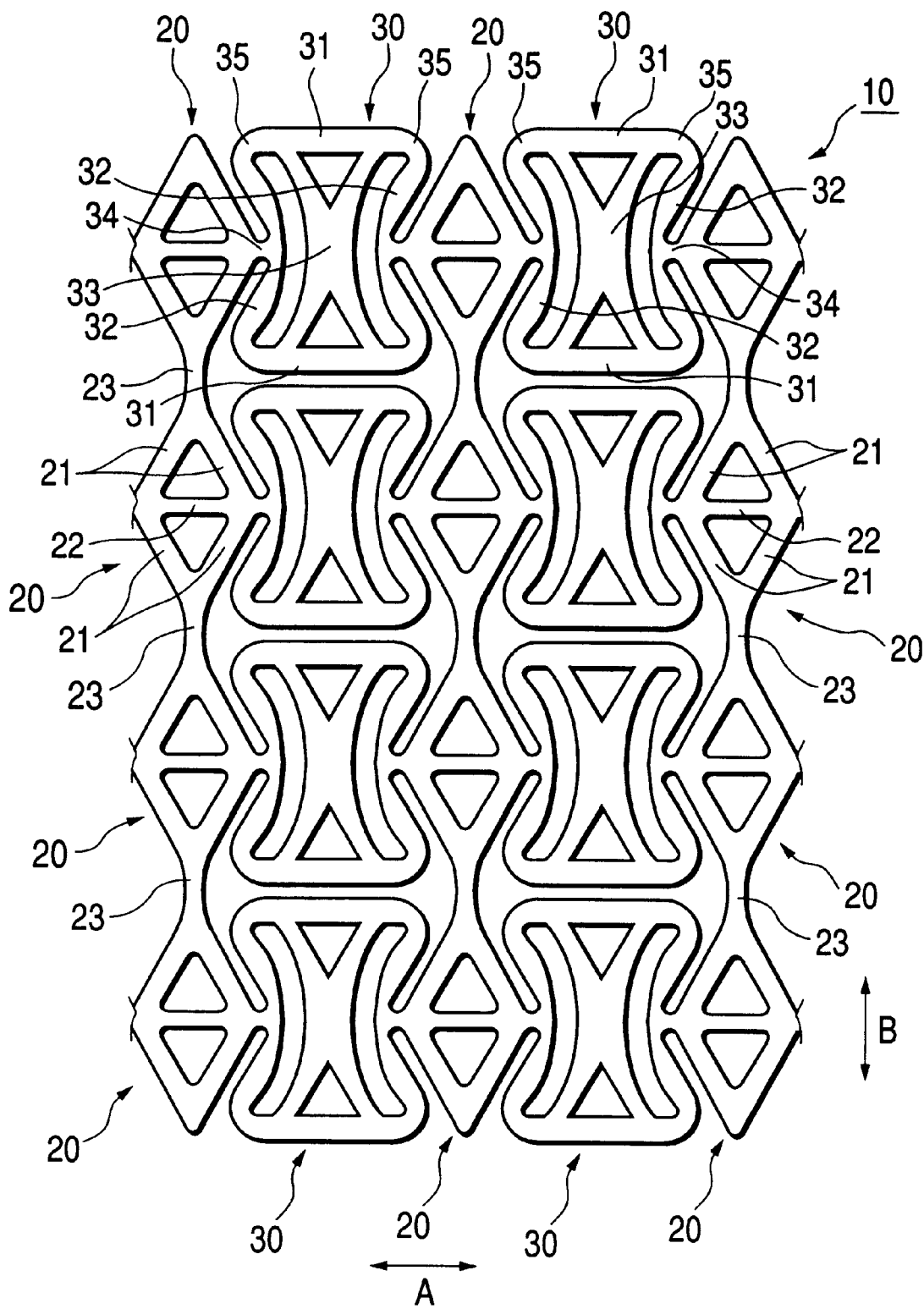
FIG. 2 is a fragmentary developed view of the same stent in its diameter-reduced state.
Figure 3:
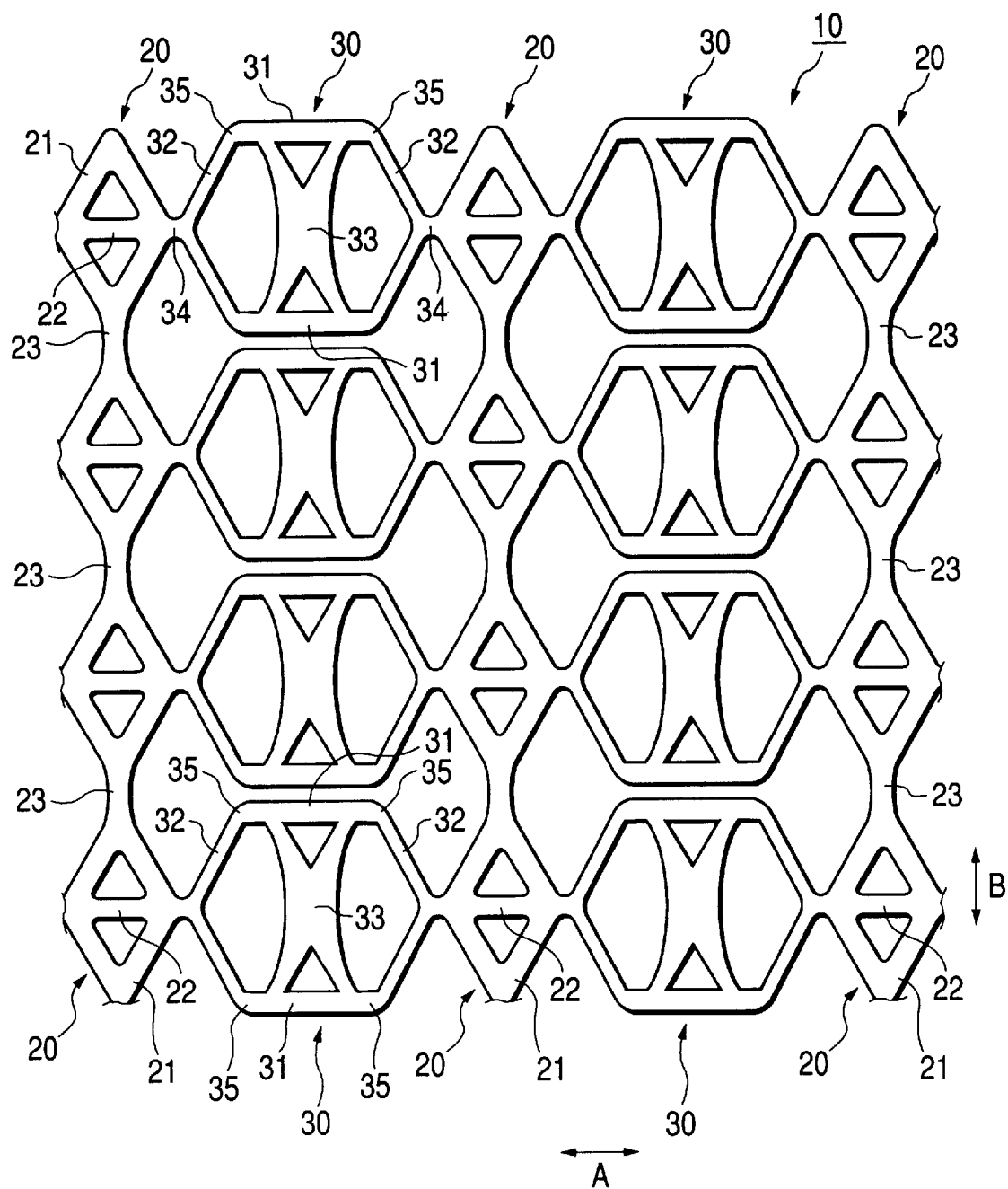
FIG. 3 is a fragmentary developed view of the same stent in its diameter-expanded state.

In FIGS. 1 to 3, there is shown an embodiment of a stent according to the present invention. FIG. 1 is a perspective view of the stent in its diameter-reduced state, FIG. 2 is a fragmentary developed view of the stent in its diameter-reduced state, and FIG. 3 is a fragmentary developed view of the stent in its expanded state.

This stent 10 has been formed by cutting a metallic cylinder member into a particular pattern, as previously described, and generally forms a cylindrical shape. The pallern is of an annular shape in which two kinds of frame-like portions, i.e., unexpandable portions 20 and expandable portions 30, are alternately connected together in a circumferential direction and the plurality of annular portions thereof are connected together in an axial direction.

Each of the unexpandable portions 20 is comprised of a frame surrounded by four sides 21 and having its opposed corner portions turned in a circumferential direction A and an axial direction B, and a beam 22 connecting the corner portions of this frame which are opposed to the circumferential direction A together, and the sides 21 and the beam 22 are connected together into a triangular shape to form a triangular truss structure, and forms a shape which is deformed neither in the circumferential direction A nor in the axial direction B.

The plurality of unexpandable portions 20 are connected together in the axial direction B through connecting portions 23 to constitute an unexpandable column in which wide portions and narrow portions in the circumferential direction are alternately repeated in the axial direction. The unexpandable column imparts bendability in the axial direction. Further, a plurality of said unexpandable columns are arranged at predetermined intervals in the circumferential direction, whereby a space in which narrow spaces and wide spaces are alternately repeated in the axial direction is formed between them.

Each of the expandable portions 30 is comprised of a frame surrounded by a pair of sides 31 extending along the circumferential direction A and opposed to each other in the axial direction B and a pair of sides 32 extending along the axial direction B and opposed to each other in the circumferential direction A, and an X-shaped beam 33 connecting the two sides 31 of this frame which are opposed to each other in the axial direction B together. The pair of sides 32 opposed to each other in the circumferential direction A are inwardly curved in the diameter-reduced state of FIGS. 1 and 2, and are outwardly curved in the diameter-expanded state of FIG. 3. In other words, the sides 31 extending along the circumferential direction A and the sides 32 extending along the axial direction B are designed to form an acute angle in the diameter-reduced state and to form an obtuse angle in the diameter-expanded state.

In the diameter-reduced state of FIGS. 1 and 2, the pair of sides 32 opposed to each other in the circumferential direction A have their intermediate portion connected to the wide portions (i.e., the corner portions opposed to each other in the circumferential direction) of the unexpandable portion 20 in the narrow space between the unexpandable columns through a connecting portion 34, and have their opposite ends extended so as to widen the distance therebetween toward the wide space between the unexpandable columns, that is, are designed such that in the diameter-reduced state, the width between the ends of the side 32 (i.e., the length of the side 31 in the circumferential direction) becomes greater than the width between the intermediate points of the sides 32 in the circumferential direction, whereby the arrangement density of the unexpandable portions 20 and expandable portions 30 may be made as high as possible.

Thus, the expandable portions 30 and the unexpandable portions 20 are alternately connected together in the circumferential direction and the unexpandable portions 20 are connected together in the axial direction through the connecting portions 23, whereby a predetermined number of annular members are connected together in the axial direction and a cylindrical stent 10 is constructed.

In order to facilitate expansion, it is preferable that the intermediate portions of the sides 32 of the expandable portions 30 opposed to each other in the circumferential direction in which the connecting portions 34 are provided, and the corner portions 35 between the sides 32 of the expandable portions 30 opposed to each other in the circumferential direction and the sides 31 thereof opposed to each other in the axial direction be narrower in line width than the other portions. Specifically, it is preferable that the line width of the above-mentioned portions be 5–300 $\mu$m and the line width of the other portions be 10–500 $\mu$m.

Also, it is preferable that in order to be capable of imparting a holding force necessary for the expansion of a tubular organ and not to spoil the flexibility of the stent during the insertion thereof, the thickness of the stent 10 be 5–200 μm. Also, the diameter and length of the stent 10 can be suitably determined depending on the location to which it is applied, and usually it is preferable that the diameter be 2–10 mm and the length be 5–100 mm.

Further, it is preferable that the surface of the stent 10 be covered with resin of the polyethylene fluoride origin, resin containing heparin, hydrophilic resin or the like to prevent thrombi from adhering thereto.

How to use this stent 10 will now be described with respect to an example in which the stent is applied to the strictured portion of a blood vessel.

A guide catheter is first inserted into a blood vessel through the skin by the well-known Seldinger method and the tip end portion thereof is made to reach the vicinity of the strictured portion of the blood vessel. The stent 10 is then mounted on the outer periphery of the balloon at the tip end portion of a balloon catheter in the diameter-reduced state thereof, and the balloon catheter is directed into the blood vessel through the guide catheter.

The balloon catheter is further pushed forward with a guide wire inserted into the balloon catheter as a guide, and the stent 10 mounted on the tip end portion thereof is disposed in the strictured portion. In that state, a liquid such as physiological brine is poured into the balloon through the balloon catheter to thereby inflate the balloon and expand the stent 10.

Thereafter, the liquid in the balloon is drawn out to thereby deflate the balloon, and the balloon catheter is drawn out of the inner periphery of the stent 10 and the stent 10 is detained. Thus, the strictured portion of the blood vessel is expanded by the stent 10 and the prevention or remedy of myocardial infarction, brain infarction, etc. can be done.

This stent 10 can uniformly hold the inner wall of a tubular organ such as a blood vessel with a wide area of contact because the unexpandable portions 20 are disposed between adjacent ones of the expandable portions 30 and both of the expandable portions 30 and the unexpandable portions 20 form a frame-like shape having a predetermined area, and the undesirable possibility of the tissue of the inner wall propagating therein from the gap of the stent 10 and causing reblockading becomes small.

Also, the unexpandable portions 20 are deformed neither in the circumferential direction A nor in the axial direction B and the expandable portions 30 have their sides 32 opposed to each other in the circumferential direction inwardly curved during the reduction of the diameter and outwardly curved during the expansion, and the axial length thereof before and after the expansion does not change. Therefore, the stent 10 undegoes very little change in its axial length before and after the expansion thereof and thus, an expanding operation can be performed easily and reliably. Further, design is made such that the sides 32 extending along the axial direction and opposed to each other in the circumferential direction and the sides 32 extending along the circumferential direction and opposed to each other in the axial direction form an acute angle in the diameter-reduced state of the stent and form an obtuse angle in the diameter-expanded state of the stent and therefore, the degree of diameter expansion can be adopted greatly and the amount of diameter expansion of the entire stent can be secured sufficiently.

Figure 4:
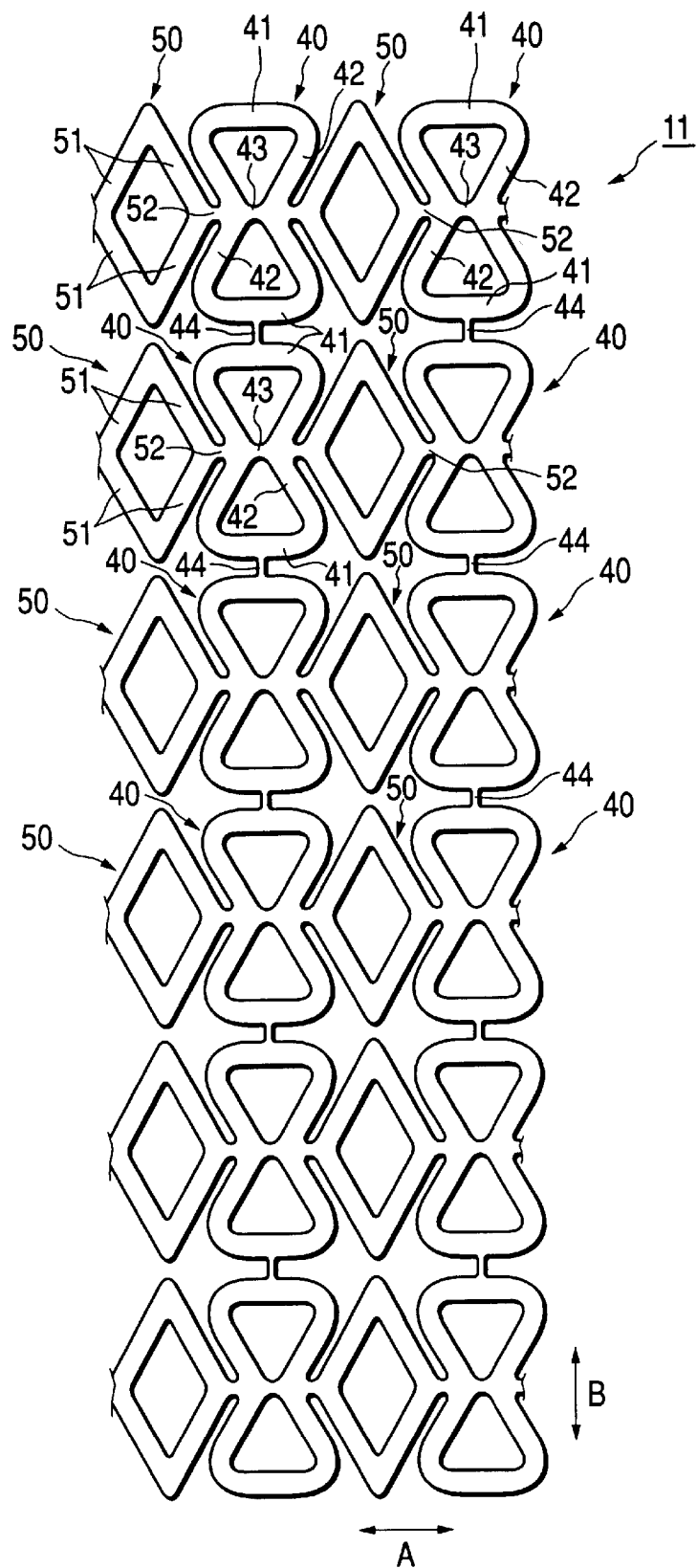
FIG. 4 is a fragmentary developed view showing another embodiment of the stent of the present invention in its diameter-reduced state.
Figure 5:
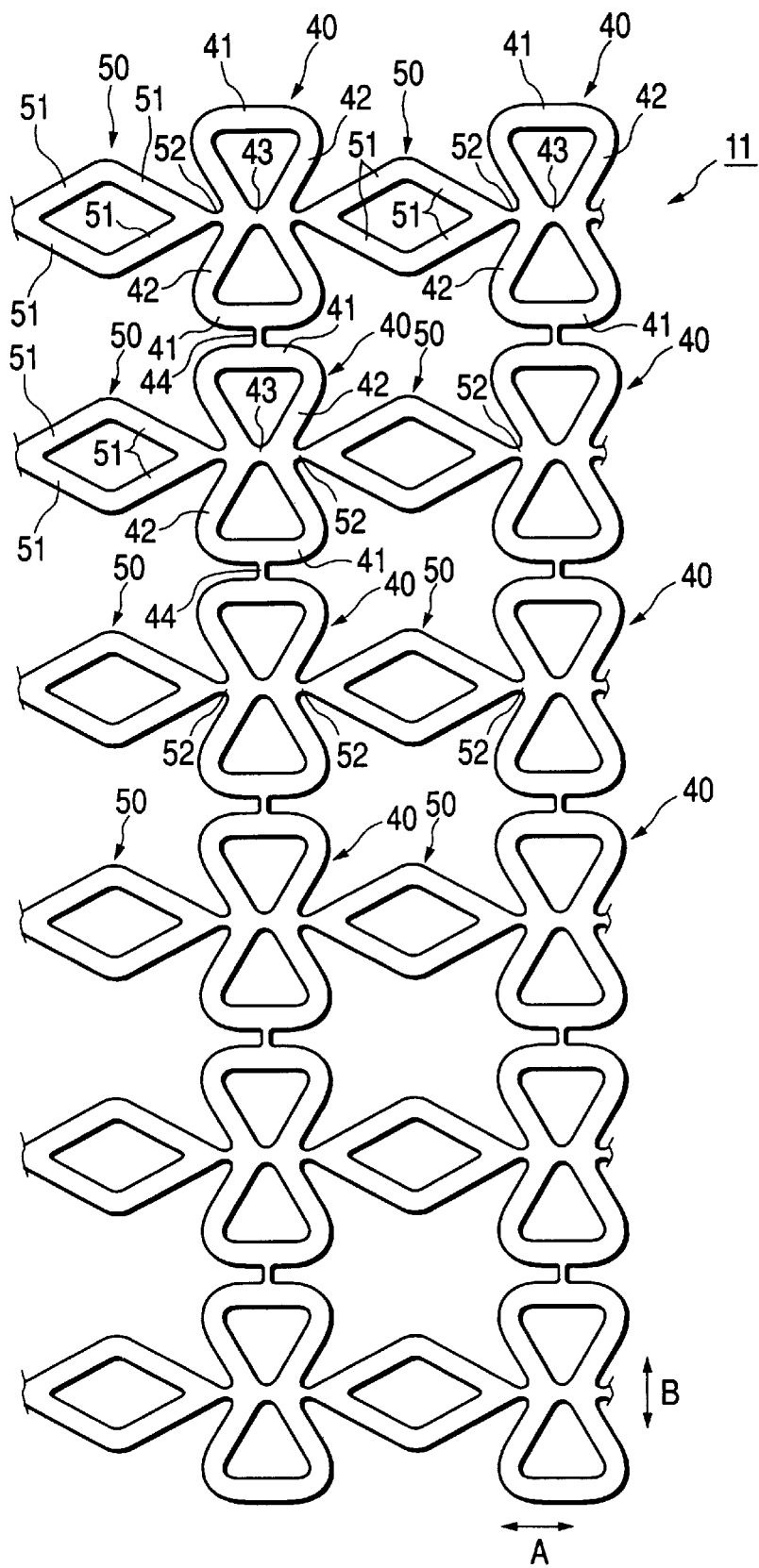
FIG. 5 is a fragmentary developed view of the same stent in its expanded state.

FIGS. 4 and 5 show another embodiment of the stent according to the present invention. FIG. 4 is a fragmentary developed view of the stent in its diameter-reduced state, and FIG. 5 is a fragmentary developed view of the stent in its expanded state.

This stent 11 has also been formed by cutting a metallic cylinder member into a particular pattern, and generally forms a cylindrical shape. The stent 11 is of a shape in which two kinds of frame-like portions, i.e., unexpandable portions 40 and expandable portions 50, are alternately connected together in the circumferential direction to thereby form an annular shape and a plurality of such annular portions are connected together in the axial direction.

Each of the unexpandable portions 40 is comprised of a frame surrounded by sides 41 extending along the circumferential direction A and opposed to each other in the axial direction B and sides 42 opposed to each other in the circumferential direction A and inwardly curved, and a beam 43 connecting the intermediate portions of the sides 42 of this frame opposed to each other in the circumferential direction A together, and in other words, forms a shape in which triangular frames are turned upside down and connected together. A plurality of unexpandable portions 40 are arranged in the axial direction through connecting portions 44, which impart the bendability of the stent 11 in the axial direction.

Each of the expandable portions 50 is of a lozenge-shape in which it is surrounded by four sides 51 and corners opposed to each other are disposed in the axial direction B and the circumferential direction A. The expandable portions 50 are deformed so that in the diameter-reduced state shown in FIG. 4, the diagonal linking the corner portions opposed to each other in the axial direction B together may become longer than the diagonal linking the corners opposed to each other in the circumferential direction A together and in the expanded state shown in FIG. 5, the diagonal linking the corner portions opposed to each other in the axial direction B together may become shorter than the diagonal linking the corner portions opposed to each other in the circumferential direction A together.

Also, each expandable portion 50 is connected to the adjacent unexpandable portion 40 through a connecting portion 52. A plurality of expandable portions 50 and unexpandable portions 40 are alternately connected together in the circumferential direction A to form an annular shape, and a plurality of such annular portions are connected together in the axial direction by the connecting portions 44 of the unexpandable portions 40, whereby a generally cylindrical stent 11 is constructed.

When a pressure force is imparted to this stent 11 from the inside thereof by the balloon catheter, the lozenge-shape of the expandable portions 50 is deformed as previously described and the stent 11 is deformed so as to be widened in the circumferential direction A. At this time, the axial length of each expandable portion 50 becomes shorter but the axial length of each unexpandable portion 40 is not changed and therefore, the axial length of the stent 11 is not changed. Also, both of the unexpandable portions 40 and the expandable portions 50 form frame-like shapes and support the inner wall of a tubular organ with a wide area and therefore, the tissue of the inner wall of the tubular organ can be prevented from coming into the inside the stent and from growing there, so that the reconstriction can be prevented.

As described above, according to the present invention, both of the expandable portions and the unexpandable portions form frame-like shapes and in a state in which the stent has been expanded, the shape of the unexpandable portions can be maintained at least partially to have the same shape as before expansion and therefore, a soft inner wall of a tubular organ can be satisfactorily held or supported by the stent while maintaining the density of arrangement of the plural sides constituting the frame-like shapes upon retention of the stent in the inner wall of the tubular organ, so that the unexpandable portions of the frame-like shape is prevented from getting into the inner wall of the tubular organ to avoid an occurrence of reconstriction of the tubular organ.

What is claimed is:

1. A stent having a cylindrical shape, said cylindrical shape having a diameter adjustable between an expanded state and a reduced state, said stent comprising:

frame-like unexpandable portions incapable of being expanded in a circumferential direction; and frame-like expandable portions capable of being expanded in the circumferential direction;

wherein said unexpandable portions and said expandable portions are alternately connected together in the circumferential direction, each of said unexpandable portions comprising a triangular frame, said frame having a portion which extends along the circumferential direction of said stent.

2. A stent according to claim 1, wherein each of said expandable portions is constructed into a frame-like shape by first sides extending along the circumferential direction and opposed to each other in the axial direction, and second sides extending in the axial direction and opposed to each other in the circumferential direction, and said frame-like shape is designed such that in the diameter-reduced state of said stent, the second sides of said frame-like shape are curved inwardly thereof and that in the diameter-expanded state of said stent, the second sides of said frame-like shape are curved outwardly thereof.

3. A stent according to claim 2, wherein an X-shaped beam connecting said first sides opposed to each other in the axial direction together is provided in the interior of the frame of each of said expandable portions.

4. A stent according to claim 1, wherein each of said expandable portions is constructed into a frame-like shape by first sides extending along the circumferential direction and opposed to each other in the axial direction, and second sides coupled to said first sides, said second sides extending in the axial direction and opposed to each other in the circumferential direction, and said frame-like shape is designed such that in the diameter-reduced state of said stent, said second sides are displaced relative to said first sides so that the first side and the second side of said frame-like shape may form an acute angle and the first side and the second side of said frame-like shape may form an obtuse angle, whereby said stent is expanded in its diameter.

5. A stent according to claim 2, wherein the portions of the triangular frames of said unexpandable portions extending along the circumferential direction and the second sides of the frames of said expandable portions, are connected together.

6. A stent according to claim 4, wherein the portions of the triangular frames of said unexpandable portions extending along the circumferential direction are connected to the second sides of the frame-like shapes of said expandable portions.

7. A stent according to claim 4, wherein an X-shaped beam connecting said first sides opposed to each other in the axial direction together is provided in the interior of the frame of each of said expandable portions.

8. A stent having a cylindrical shape, said cylindrical shape having a diameter adjustable between an expanded state and a reduced state, said stent comprising:

frame-like unexpandable portions incapable of being expanded in a circumferential direction; and frame-like expandable portions capable of being expanded in the circumferential direction;

wherein said unexpandable portions and said expandable portions are alternately connected together in the circumferential direction, each of said expandable portions being constructed into a frame-like shape by first sides extending along the circumferential direction and opposed to each other in the axial direction, and second sides extending in the axial direction and opposed to each other in the circumferential direction, said frame-like shape being designed such that in the diameter-expanded state of said stent, the second sides of said frame are outwardly curved, and wherein an X-shaped beam connecting said first sides together is provided in the interior of the frame of each of said expandable portions.

9. A stent having a cylindrical shape, said cylindrical shape having a diameter adjustable between an expanded state and a reduced state, said stent comprising:

frame-like unexpandable portions incapable of being expanded in a circumferential direction; and frame-like expandable portions capable of being expanded in the circumferential direction;

wherein said unexpandable portions and said expandable portions are alternately connected together in the circumferential direction, each of said expandable portions being constructed into a frame-like shape by first sides extending along the circumferential direction and opposed to each other in the axial direction, and second sides extending in the axial direction and opposed to each other in the circumferential direction, said frame-like shape being designed such that in the diameter-reduced state of said stent, said second sides are displaced relative to said first sides so that the first side and the second side of said frame-like shape may form an acute angle and the first side and the second side of said frame-like shape may form an obtuse angle, whereby said stent is expanded in its diameter, and wherein an X-shaped beam connecting said first sides together is provided in the interior of the frame-like shape of each of said expandable portions.

10. A stent having a cylindrical shape, said cylindrical shape having a diameter adjustable between an expanded state and a reduced state, said stent comprising:

frame-like unexpandable portions incapable of being expanded in a circumferential direction; and frame-like expandable portions capable of being expanded in the circumferential direction;

wherein said unexpandable portions and said expandable portions are alternately connected together in the circumferential direction, wherein said unexpandable portions are directly connected to each other in an axial direction to form a column of unexpandable portions, whereby unexpandable portion columns and expandable portion columns extending in the axial direction are alternately disposed in the circumferential direction.

11. A stent according to claim 10, wherein each of said unexpandable portions comprises a triangular frame, a portion of which extends along the circumferential direction of said stent.

12. A stent according to claim 10, wherein each of said expandable portions is constructed into a frame-like shape by first sides extending along the circumferential direction and opposed to each other in the axial direction, and second sides extending in the axial direction and opposed to each other in the circumferential direction, and said frame-like shape is designed such that in the diameter-expanded state of said stent, the second sides of said frame-like shape are outwardly curved.

13. A stent according to claim 12, wherein each of said unexpandable portions comprises a triangular frame, a portion of which extends along the circumferential direction of said stent.

14. A stent according to claim 10, wherein each of said expandable portions is constructed into a frame-like shape by first sides extending along the circumferential direction and opposed to each other in the axial direction, and second sides extending in the axial direction and opposed to each other in the circumferential direction, and said frame-like shape is designed such that in the diameter-reduced state of said stent, said second sides are displaced relative to said first sides so that the first side and the second side of said frame-like shape may form an acute angle and the first side and the second side of said frame-like shape may form an obtuse angle, whereby said stent is expanded in its diameter.

15. A stent according to claim 14, wherein each of said unexpandable portions comprises a triangular frame, a portion of which extends along the circumferential direction of said stent.

* * * * *